United States Patent [19]

Kleinberg et al.

[11] Patent Number: 4,768,238
[45] Date of Patent: Sep. 6, 1988

[54] BIFURCATED SALIVA COLLECTOR

[75] Inventors: Israel Kleinberg, Smithtown; Leo M. Sreebny, East Setauket, both of N.Y.

[73] Assignee: Interstate Drug Exchange, Amityville, N.Y.

[21] Appl. No.: 46,837

[22] Filed: May 4, 1987

[51] Int. Cl.⁴ ............................................. A61J 19/00
[52] U.S. Cl. ........................................ 4/258; 4/267; 4/144.1; 128/762; 128/760
[58] Field of Search ...... 4/259, 258, 267, 144.1–144.4; 128/762, 760, 771, 777, 774, 3; 206/459; 215/6; 220/408; 73/864.91; 604/317; 435/296, 30; 422/99, 101, 102

[56] References Cited

U.S. PATENT DOCUMENTS

| | | | |
|---|---|---|---|
| 2,171,748 | 9/1939 | Hamilton | 4/267 |
| 3,362,315 | 1/1968 | Buechner | 220/408 X |
| 3,499,327 | 3/1970 | Lane, Jr. | 4/144.1 X |
| 3,518,164 | 6/1970 | Andelin et al. | 4/144.1 X |
| 3,774,455 | 11/1973 | Seidler et al. | 128/771 X |
| 3,831,446 | 8/1974 | Dye | 128/771 X |
| 3,871,230 | 3/1975 | Dye et al. | 128/771 X |
| 4,042,337 | 8/1977 | Griffith | 128/762 |
| 4,503,572 | 3/1985 | Dawson | 4/259 X |
| 4,580,577 | 4/1986 | O'Brien | 604/296 |

Primary Examiner—Henry K. Artis
Attorney, Agent, or Firm—Lackenbach Siegel Marzullo & Aronson

[57] ABSTRACT

This patent relates to a bifurcated vessel for the collection of saliva comprising:

(a) a receptacle open at one end and divided into two chambers for holding liquid;

(b) an open edge portion angularly disposed integral with one of said chambers to constitute a flared funnel to said chamber; and (c) a second open edge portion angularly disposed to and integral with the other of said two chambers to constitute a flared funnel.

13 Claims, 1 Drawing Sheet

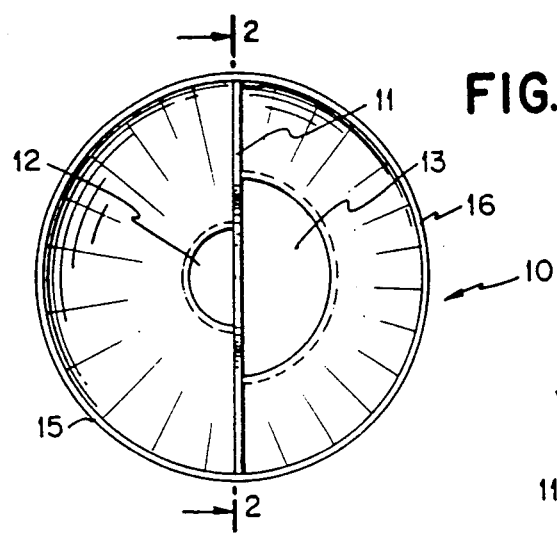
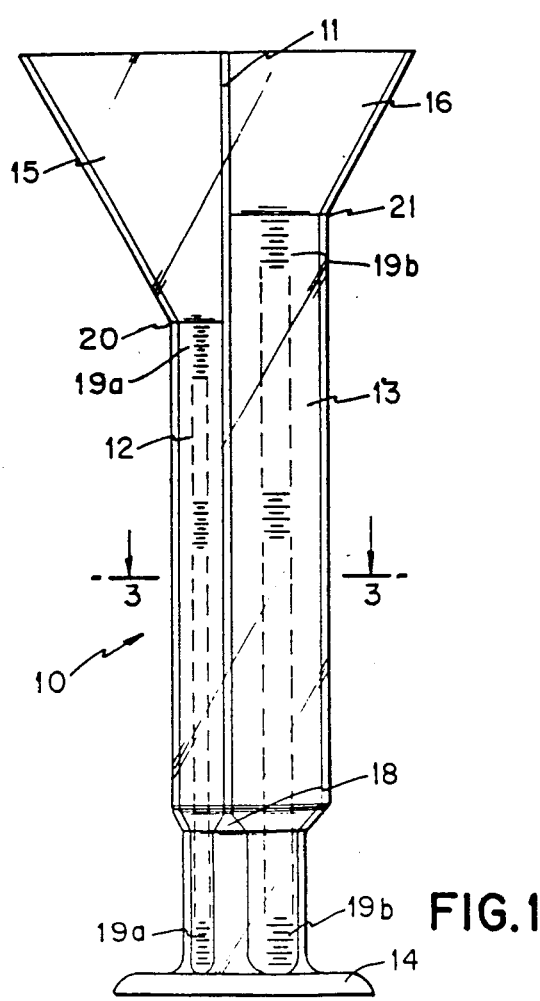
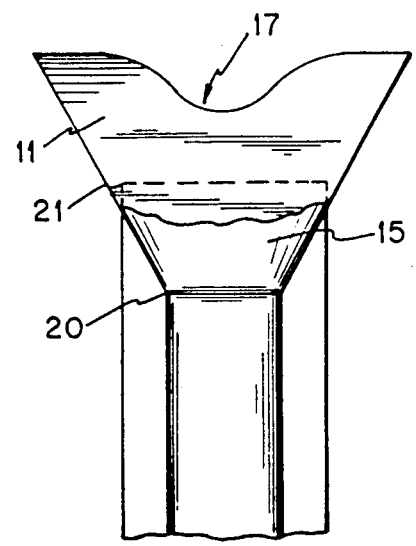
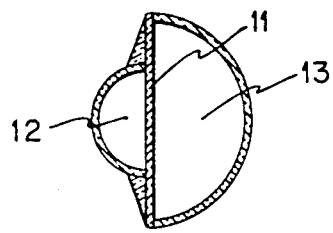

BIFURCATED SALIVA COLLECTOR

FIELD OF THE INVENTION

This invention relates to xerostomia, or dry mouth. Xerostomia has a multitude of structural and/or systemic causes and associations such as severe dental caries, periodontal disease, mucositis, salivary gland aplasia, disturbed oral sensation, and altered taste function. Additionally, xerostomia is a common side effect in the administration of over 400 clinical drugs as well as radiation treatment to the head or neck region. Among the many drugs which can cause xerostomia in certain patients are the major antihypertensives, antidepressants, antispasmodics, diuretics, muscle relaxants, antipsychotics, appetite depressants, and therapeutics for Parkinson's disease. Many patients suffering from rheumatoid arthritis also exhibit decreased secretion of saliva. Psychological stress can also lead to symptoms of xerostomia.

For patients whose dry mouth symptoms are secondary, increased consumption of liquids, chewing gum, and sucking flavored lozenges often suffice to maintain salivation between meals. At meal times the presence and eating of food often stimulates secretion of sufficient saliva for comfort and digestion.

Sialometry, measurement of the flow rate of saliva, is a sensitive index of potential or existing oral or systemic maladies. It is useful in many instances for the dentist or physician to know both the unstimulated and stimulated rates of salivation. This invention relates to apparatus for unambiguously measuring the flow of saliva under both unstimulated and stimulated conditions.

BACKGROUND OF THE INVENTION AND DISCUSSION OF THE PRIOR ART

The general methods for collecting human saliva has been reviewed in the American Journal of Otolaryngology, volume 4, p. 288, 1983 by Navazesh and Ship.

An apparatus for collecting saliva comprising a container with a threaded open end and a conical closed end, a threaded funnel for sometime use on the open end or a threaded cap to seal such, and a base for holding the closed conical end has been disclosed by Fay in U.S. Pat. No. 4,589,548 issued May 20, 1986.

An apparatus for sequentially collecting saliva in a flavored absorbent, masticated sponge and then pressing the sample out with a piston plunger through a small hole, through which the sponge cannot pass but the sample can, was shown Apr. 8, 1986 by O'Brien et al. in U.S. Pat. No. 4,580,577.

A specimen collection and transport system was disclosed by Schlesinger in U.S. Pat. No. 4,283,498. The system comprises a specimen receptacle having a closed bottom and an open top, a conduit to the receptacle, a base to hold the conical closed end, and a protective covering so that the specimen can be transported.

A collection apparatus for saliva is shown by Andelin et al. in U.S. Pat. No. 3,518,164. This apparatus also has a receptacle closed at one end and open at the other, a funnel and discharge tube leading to the receptacle, a funnel cover, an outer protective body also functioning as a support, and a threaded cap.

OBJECTS OF THE INVENTION

It is an object of the present invention to provide an apparatus for the collection of saliva under unstimulated and stimulated conditions.

It is a further object of this invention to measure and compare unstimulated and stimulated saliva flow as a diagnostic tool.

It is another object of the invention to provide samples for analysis and comparison of the chemical and physical properties of unstimulated and stimulated saliva.

It is yet another object of the invention to separate cellular and particulate components from saliva, so that the supernatant fluid may be easily analyzed for various components whose absence or presence may show different pathological disorders.

Other objects of the invention will be apparent to those skilled in the art.

SUMMARY OF THE INVENTION

The above and other objects are surprisingly fulfilled by a bifurcated vessel for the collection of stimulated and unstimulated amounts of saliva. The bifurcated vessel comprises:

(a) a vertical receptacle open at the top and divided into two parallel chambers for holding liquid;
(b) an upper edge portion angularly disposed to and integral with one of the parallel chambers to constitute a flared funnel to that chamber;
(c) a second upper edge portion angularly disposed to and integral with the second parallel chamber to constitute a flared funnel; and
(d) a base closing off the bottom of both parallel chambers, whereby saliva may be separately collected at two different times and compared volumetrically and chemically as well as separated into fractions for chemical analysis.

Once the volume of saliva has been determined, one can carry out analyses on the two salivas while they remain in the chambers.

BRIEF DESCRIPTION OF THE DRAWINGS

FIG. 1 is a side elevational view of one embodiment of the present invention.

FIG. 2 is a vertical section view through the line 2—2 of FIG. 4.

FIG. 3 is a cross section view taken through the line 3—3 of FIG. 1.

FIG. 4 is a top plan view of the embodiment of FIG. 1.

DESCRIPTION OF THE PREFERRED EMBODIMENTS

The unstimulated, whole mouth saliva production of a healthy adult can range from about 0.08 to about 1.85 ml/min and averages about 0.3 ml/min. For a six-minute test period, the unstimulated normal sample would be about 1.8 to 3 ml. Actually "unstimulated" is a misnomer really meaning "minimally" stimulated.

Stimulated, whole mouth production is achieved by gustatory (e.g. citric acid) or masticatory (e.g. inert gum, rubber band, paraffin wax) means and increases the rate normally three-to six-fold to about 6–12 ml for a six-minute test period. A "six minute" test period generally means three, two-minute periods by expectoration with swallowing permitted in between.

Therefore, although the size of the chambers in the apparatus of the present invention may vary widely, a preferred embodiment would have an unstimulated collection chamber, preferably calibrated per 0.1 ml. of about 4 ml., and a stimulated collection chamber from about 10 to about 15 ml., calibrated preferably per 0.1 ml.

Of course, for patients suffering from xerostomia for primary (organic) or secondary (systemic or psychological) reasons the salivary flow may be reduced to almost or actually nothing. A patient is labeled xerostomic at an unstimulated production of less than about 0.6 ml. in six minutes or a stimulated production less than about 4 ml. in a six-minute test period. This boundary between normal and unhealthy may be indicated by a colored or other differentiating marking on the apparatus of this invention. Also, it is convenient that the dimensions for a single two-minute volume be differentiated.

The collector of the present invention may be constructed of glass, crystal, plastic or any other convenient material. A transparent material is preferred but is not necessary.

The volume of the larger (stimulated flow) chamber of the collector preferably is about four times that of the smaller (unstimulated flow) chamber, but this ratio is not necessary. Preferably the cross-sectional area of the larger chamber is also about four times that of the smaller chamber, so that either a normal or abnormal flow will register at about the same height on the calibrated device. It is preferable, but not necessary, that the lower section of the bifurcated device be smaller in cross-section than the middle and upper sections of the device, so that small flows can be measured with high accuracy. It is also convenient, but not necessary, that this lower section of the device be constructed with thicker material to gain higher structural strength.

Preferably, but not necessarily, the upper section of the receptacle is flared to form a funnel. This enables the patient to expectorate into the receptacle easier and guarantees that all the saliva be measured. It is preferable that the funnel extend all around the upper lip and that the angle of the funnel be uniform around the entire circumference. Since the "stimulated" side of the device is preferably larger in cross-section than the "unstimulated" side of the device, the angular portion of the unstimulated side will extend lower down the device if a uniform flare is to be maintained, as shown in FIG. 1.

Preferably, but not necessarily, the upper end of the divider between the two chambers of the receptacle extends above the preferably flared upper edge of the receptacle. This ensures that all the saliva is collected. Furthermore, so that the patient being tested can come even closer to the flared, divided top of the receptacle, a notch to accommodate the nose is made in the upper section of the divider, as shown in FIG. 2.

FIG. 1 shows an embodiment of the bifurcated saliva collector of the present invention, generally indicated as 10. The tubular receptacle is divided by inner wall 11 into a smaller chamber 12, intended for collection of unstimulated saliva, and larger chamber 13, intended for collection of stimulated flow. The bifurcated collector is closed off and supported by base 14. Divider 11 is reinforced near the bottom up to a point 18, which is conveniently the point where chambers 12 and 13 are of smaller diameter so that the accuracy of measurements of small volumes is higher. Preferably the entire receptacle is calibrated by markings 19a and 19b into convenient volumes such as milliliters. Preferably the two sides of the upper edge are uniformly flared at 15 and 16 to create a funnel to help receive all the saliva. The uniform flare of 15 and 16 at the upper edge requires that the angulation of the small diameter side end lower at 20 than that of the large diameter side at 21.

In FIG. 2 the top of divider 11 is shown with a notch for the nose 17.

In FIG. 3 the cross-section of the receptacle at the line 3—3 in FIG. 1 is shown with the relative size of small diameter 12 to that of larger diameter 13, as separated by divider 11.

In FIG. 4 the top plan view shows the uniform flare of upper edges 15 and 16 with the top of tubular chambers 12 and 13.

Many other embodiments will occur to those skilled in the art, but such will be within the scope of Letters Patent based on the following claims:

We claim:

1. A bifurcated vessel for the collection of saliva and used to measure different types of saliva flow comprising:
   (a) a receptacle open at one end and divided into two chambers for holding liquid;
   (b) an open edge portion angularly disposed integral with one of said chambers to constitute a flared funnel to said chamber;
   (c) a second open edge portion angularly disposed to and integral with the other of said two chambers to constitute a flared funnel; and
   (d) a divider between the two chambers, the upper end of said divider extending to or above the upper edge of the receptacle.

2. The vessel of claim 1, wherein said vessel is vertical and includes base means.

3. The vessel of claim 2, wherein said base is in the form of a flanged circular shape, which closes off the other end of the vessel.

4. The vessel of claim 1, wherein the chambers are parallel.

5. The vessel of claim 1, wherein the chambers are unequal in size.

6. The vessel of claim 1, wherein the cross-section of each parallel chamber is in the shape of a half-circle.

7. The vessel of claim 1, wherein the angular disposition of the edge portions for the two chambers is different.

8. The vessel of claim 1, wherein each of the two chambers is individually calibrated for volume.

9. The vessel of claim 1, wherein the closed end portions of the two chambers is smaller in cross-section than the remainder of the two portions.

10. The vessel of claim 5, wherein one chamber is approximately four times larger than the other chamber.

11. The vessel of claim 1, wherein the divider is reinforced near the bottom thereof.

12. A bifurcated vessel for the collection of saliva and used to measure different types of saliva flow comprising:
   (a) a receptacle open at one end and divided into two chambers for holding liquid;
   (b) an open edge portion angularly disposed integral with one of said chambers to constitute a flared funnel to said chamber;
   (c) a second open edge portion angularly disposed to and integral with the other of said two chambers to constitute a flared funnel; and (d) said vessel being vertical and including base means, wherein said base means is in the form of a flanged circular shape, which closes off the other end of the vessel.

13. A bifurcated vessel for the collection of saliva and used to measure different types of saliva flow comprising:
   (a) a receptacle open at one end and divided into two chambers for holding liquid;
   (b) an open edge portion angularly disposed integral with one of said chambers to constitute a flared funnel to said chamber;
   (c) a second open edge portion angularly disposed to and integral with the other of said two chambers to constitute a flared funnel; and
   (d) wherein each of the two chambers is individually calibrated for volume.

* * * * *